(12) United States Patent
Zheng et al.

(10) Patent No.: US 10,898,632 B2
(45) Date of Patent: Jan. 26, 2021

(54) ADSORBING MATERIAL FOR MULTIPLE PATHOGENIC FACTORS OF SEPSIS AS WELL AS PREPARATION METHOD AND APPLICATION THEREOF

(71) Applicant: Chongqing Zhengbo Biotechnology Co. Ltd., Chongqing (CN)

(72) Inventors: Yue Zheng, Chongqing (CN); Jun Deng, Chongqing (CN); Qingguang Liu, Chongqing (CN)

(73) Assignee: Chongqing Zhengbo Biotechnology Co. Ltd., Chongqing (CN)

( * ) Notice: Subject to any disclaimer, the term of this patent is extended or adjusted under 35 U.S.C. 154(b) by 358 days.

(21) Appl. No.: 15/770,629

(22) PCT Filed: Oct. 27, 2016

(86) PCT No.: PCT/CN2016/103459
§ 371 (c)(1),
(2) Date: Apr. 24, 2018

(87) PCT Pub. No.: WO2017/071601
PCT Pub. Date: May 4, 2017

(65) Prior Publication Data
US 2019/0054227 A1    Feb. 21, 2019

(30) Foreign Application Priority Data
Oct. 29, 2015    (CN) .......................... 2015 1 0717518

(51) Int. Cl.
| A61M 1/00 | (2006.01) |
| B01J 20/00 | (2006.01) |
| A61M 1/34 | (2006.01) |
| B01J 20/26 | (2006.01) |
| B01J 20/30 | (2006.01) |
| A61M 1/36 | (2006.01) |
| A61M 1/02 | (2006.01) |
| A61M 1/38 | (2006.01) |

(52) U.S. Cl.
CPC ........ *A61M 1/3486* (2014.02); *A61M 1/0259* (2013.01); *A61M 1/34* (2013.01); *A61M 1/341* (2014.02); *A61M 1/3403* (2014.02); *A61M 1/3609* (2014.02); *A61M 1/3633* (2013.01); *A61M 1/3687* (2013.01); *A61M 1/3692* (2014.02); *A61M 1/38* (2013.01); *B01J 20/26* (2013.01); *B01J 20/30* (2013.01)

(58) Field of Classification Search
CPC ......... A61M 1/3486; B01J 20/26; B01J 20/30
See application file for complete search history.

(56) References Cited

U.S. PATENT DOCUMENTS

| 2012/0152847 A1 | 6/2012 | Falkenhagen et al. |
| 2013/0105396 A1 | 5/2013 | Falkenhagen et al. |

FOREIGN PATENT DOCUMENTS

| CN | 1864755 A | 11/2006 |
| CN | 102247817 A | 11/2011 |
| CN | 103769060 A | 5/2014 |
| CN | 105195114 A | 12/2015 |

*Primary Examiner* — Sikarl A Witherspoon
(74) *Attorney, Agent, or Firm* — Burns & Levinson LLP; Janine M. Susan

(57) ABSTRACT

An adsorbing material for multiple pathogenic factors of sepsis as well as a preparation method and an application thereof are provided. The adsorbing material is formed by coupling a carrier with good mechanical performance and blood compatibility and a ligand with the capacity to adsorb multiple pathogen-associated molecular patterns, and is capable of effectively adsorbing bacterial endotoxin, bacterial genomic DNA, peptidoglycan, lipoteichoic acid, virus RNA, and zymosan from fluids such as blood and the like, and in particular has application value in blood purification for treatment of sepsis.

8 Claims, 5 Drawing Sheets

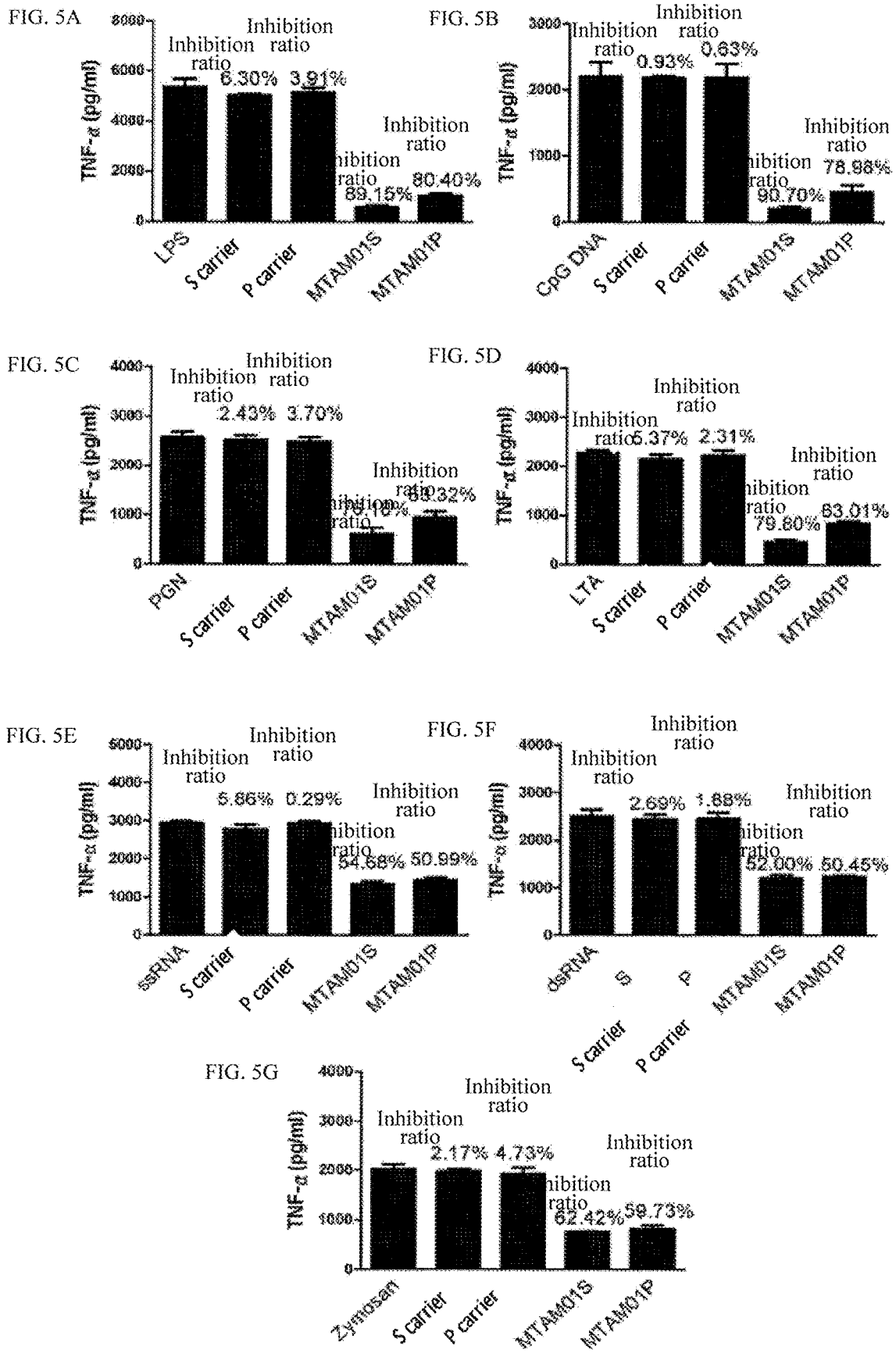

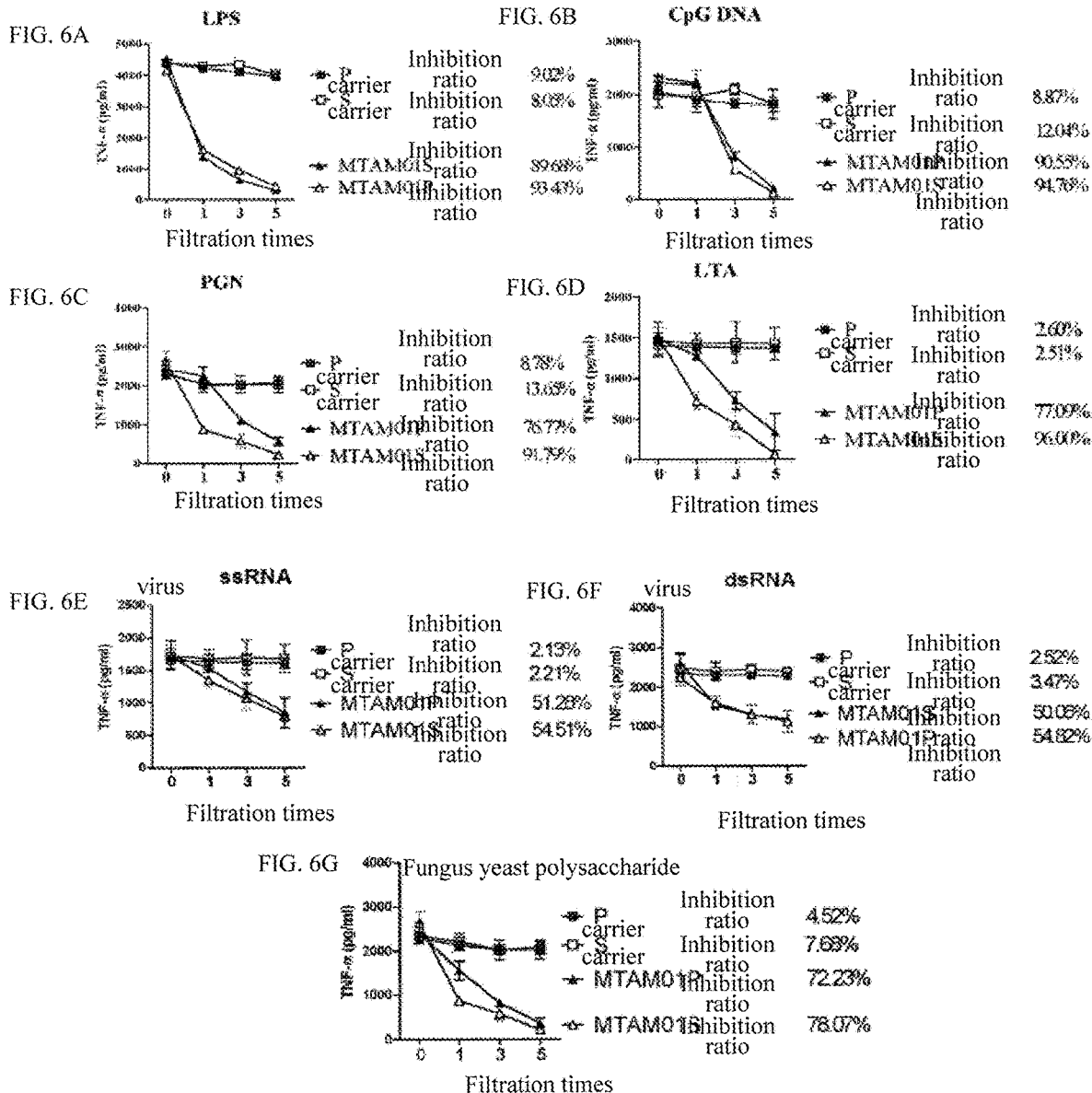

ADSORBING MATERIAL FOR MULTIPLE PATHOGENIC FACTORS OF SEPSIS AS WELL AS PREPARATION METHOD AND APPLICATION THEREOF

CROSS-REFERENCE TO RELATED APPLICATIONS

This application is the U.S. national phase entry under 35 U.S.C. § 371 of International Application No. PCT/CN2016/103459, filed Oct. 27, 2018, entitled ADSORBING MATERIAL FOR MULTIPLE PATHOGENIC FACTORS OF SEPSIS AS WELL AS PREPARATION METHOD AND APPLICATION THEREOF, which in turn claims priority to and benefit of Chinese Application No. 201510717518.1, filed Oct. 29, 2015, the contents of which are incorporated herein by reference in their entirety for all purposes.

FIELD

The present invention belongs to technical field of medicine, and particularly to an adsorbing material for multiple pathogenic factors of sepsis and a preparation method thereof as well as use in preparing a blood purification device for treatment of sepsis.

BACKGROUND

Sepsis is a systemic inflammatory response syndrome (systemic inflammatory response syndrome, SIRS) caused by infection, the number of patients in the globe every year reached up to 19,000,000, it is a major factor of the death of currently infected patients, and there is no ideal treatment so far. Research shows that the pathogen-associated molecular patterns (PAMP) released by pathogens such as bacteria, virus, fungus etc. are main pathogenic factors to induce sepsis, the currently known pathogen-associated molecular patterns mainly include endotoxin (lipopolysaccharide), bacterial genomic DNA, peptidoglycan, lipoteichoic acid coming from bacteria, virus RNA coming from virus as well as zymosan coming from fungus and the like. For this purpose, researchers have developed many antagonists, such as polymyxin B, lipid A monoclonal antibody, bactericidal/permeability increasing protein, suppressive oligonucleotide and the like, which mainly aim at the bacterial endotoxin and the bacterial genomic DNA, mostly are in preclinical or clinical studies, and has not been used clinically. In addition to the drug treatment, the blood purification is considered to be an effective means to treat sepsis. So-called blood purification is to take patients' blood out of body, and remove pathogenic factors in the blood through a specialized purification device, and thereby purify the blood and achieve the purpose of treatment. The blood purification device is generally made up of a pump, circulation tubes, blood purification as well as relevant control part and the like. Wherein, an adsorbing material with the effect of adsorbing pathogenic factors is the most core constituent part of the blood purification device.

The blood purification for treatment of sepsis is to adsorb and remove pathogen-associated molecular patterns in patients' blood using an adsorbing material with the effect of adsorbing pathogen-associated molecular patterns. Currently, an endotoxin adsorbing material Toraymyxin has been developed by Japanese researchers, which is made up of polystyrene fiber carrier and polymyxin B covalently bonded on the carrier, and has appeared on the market in Japan (1994) and Europe (2002), and is being subject to a phase III clinical trials in America. This kind of adsorbing material is capable of adsorbing endotoxin effectively, it has good biocompatibility, and is adapted to the blood purification for treatment of sepsis (Hisataka Shoji.Extracorporeal endotoxin removal for the treatment of sepsis: endotoxin adsorption cartridge (Toraymyxin). Ther Apher Dial. 2003; 7(1): 108-114.). Another example is that an invention patent ZL03144383.4 disclosed an endotoxin adsorbing material made of natural or synthetic polymer materials as carrier and dimethylamine as ligand, which could be used for hemoperfusion to remove the endotoxin in the patients' blood. An invention patent ZL03144231.5 disclosed an adsorbing material which took spherical agarose gel as carrier and was immobilized with effective amount of affinity ligand for efficiently adsorbing the endotoxin in patients' blood. An invention patent ZL200710012501.1 disclosed an adsorbing material which took agarose gel as carrier and was coupled with two groups of quaternary ammonium salt and hydrophobic molecules through spacer arm, it could be used to clear the endotoxin in blood plasma. Invention patents CN101322933B and CN101322934B both disclosed an endotoxin adsorbing material obtained by taking spherical porous cellulose as carrier and being immobilized with polymyxin B. An invention patent CN102247817B disclosed an endotoxin adsorbing material taking a molecular cluster as a functional group as well as a preparation method thereof. An invention patent PCT/AT2010/000017 disclosed an endotoxin adsorbing material which was made up of a water-insoluble porous carrier and polymyxin B immobilized on the carrier. An invention patent PCT/AT2011/000273 disclosed an endotoxin adsorbing material which was made up of a water-insoluble porous carrier as well as polymyxin B and albumin non-covalently attached to the surface of the carrier. An invention patent CN103769060A disclosed an adsorbent which took agarose gel, polyvinyl alcohol, cellulose or polystyrene as carrier and was coupled with kukoamine B, it could adsorb endotoxin, bacterial genomic DNA and peptidoglycan. However, the above-mentioned adsorbing material can only adsorb a few of pathogen-associated molecular patterns such as endotoxin, and is invalid for other pathogen-associated molecular patterns, so it is hard to exert curative effects on sepsis induced by other pathogen-associated molecular patterns. Therefore, it is very important to develop an adsorbing material with broader spectrum and stronger adsorption capacity.

SUMMARY OF THE INVENTION

The purpose of the present invention is to improve the deficiency in adsorption capacity of the existing adsorbing materials by providing an adsorbing material for multiple pathogenic factors of sepsis. The adsorbing material can effectively adsorb multiple pathogenic factors of sepsis from fluids such as blood and the like, such as bacterial endotoxin, bacterial genomic DNA, peptidoglycan, lipoteichoic acid, virus RNA, and zymosan etc, thereby treat sepsis by eliminating these pathogen-associated molecular patterns.

The technical solution of the present invention is:

A preparation method of a ligand of adsorbing materials for adsorbing multiple pathogenic factors of sepsis in fluids, has following steps:

1) In dichloromethane, compound 1 reacts with di-tert-butyl dicarbonate to generate compound 2, reaction temperature is 20~30° C., the equivalence ratio of compound 1 and di-tert-butyl dicarbonate is 1:0.5~2, reaction equation is:

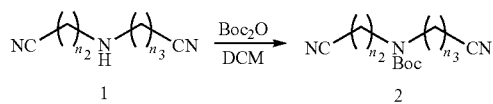

2) In a saturated solution of ammonia in methanol, compound 3 is generated from compound 2 by hydrogenation under the existence of raney nickel and hydrogen, reaction temperature is 20~50° C., pressure is 1~10 Mpa, the mass of raney nickel is 10%~50% of the mass of compound 2, reaction equation is:

3) In ethanol or methanol, compound 3 reacts with α, β-unsaturated nitrile to generate compound 4, reaction temperature is 20~50° C., the equivalence ratio of compound 3 and α, β-unsaturated nitrile is 1:2~3, reaction equation is:

4) In dichloromethane, compound 5 reacts with N-Hydroxysuccinimide to generate compound 6 under the existence of N,N'-dicyclohexylcarbodiimide and 4-dimethylaminopyridine, reaction temperature is 20~30° C., the equivalence ratio of compound 5 and N-Hydroxysuccinimide is 1:1~2, reaction equation is:

5) In dioxane, compound 4 reacts with compound 6 to generate compound 7, reaction temperature is 30~50° C., the equivalence ratio of compound 4 and compound 6 is 1:1~2, reaction equation is:

6) In dioxane, compound 7 reacts with N-Carbobenzoxyoxysuccinimide to generate compound 8, reaction temperature is 30~50° C., the equivalence ratio of compound 7 and N-Carbobenzoxyoxysuccinimide is 1:1~2, reaction equation is:

7) In ethanol or methanol, the compound 8 reacts with di-tert-butyl dicarbonate to generate compound 9 under the existence of raney nickel and hydrogen, reaction temperature is 30~50° C., the equivalence ratio of compound 8 and di-tert-butyl dicarbonate is 1:0.5~3, pressure is 1~10 Mpa, the mass of the raney nickel is 10%~50% of the mass of compound 8, reaction equation is:

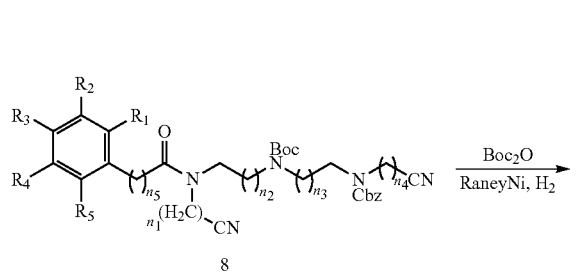

8

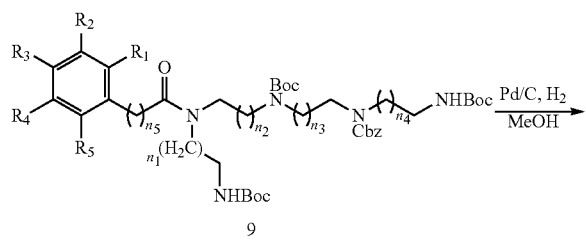

9

Palladium on carbon and hydrogen, reaction temperature is 20~50° C., pressure ranges from atmospheric pressure to 10 MPa, the mass of the Palladium on carbon is 10%~30% of the mass of compound 9, reaction equation is:

9

10

9) In dichloromethane, compound 10 reacts with succinic anhydride to generate compound 11 under the existence of 4-dimethylaminopyridine, reaction temperature is 20~30° C., the equivalence ratio of compound 10 and succinic anhydride is 1:1~2, reaction equation is:

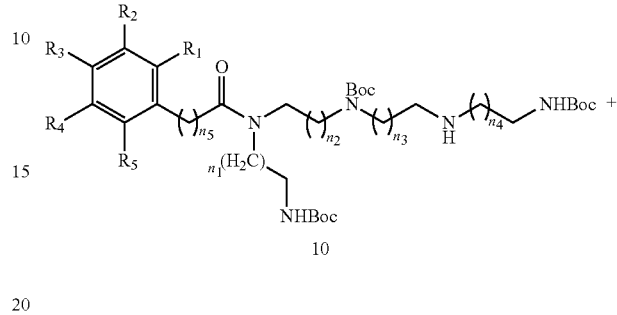

10

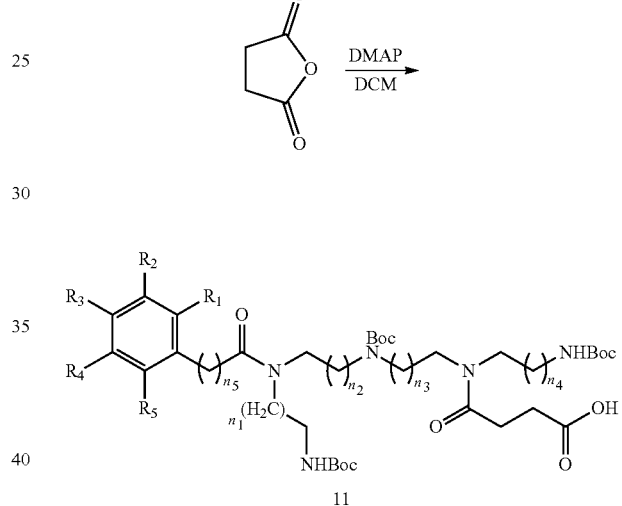

11

10) In ethyl acetate, the compound 11 reacts with N-Hydroxysuccinimide to generate compound 12, reaction temperature is 20~30° C., the equivalence ratio of compound 11 and N-Hydroxysuccinimide is 1:1~2, reaction equation is:

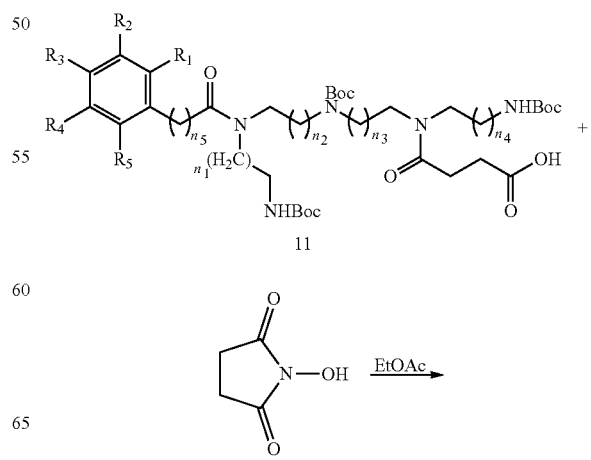

11

-continued

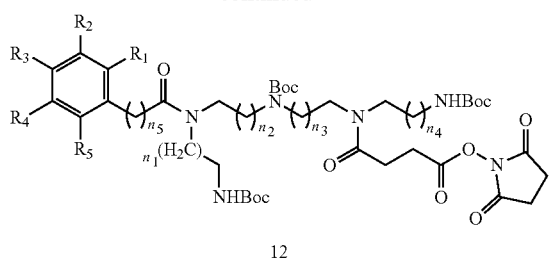

12

Above-mentioned multiple pathogenic factors of sepsis include multiple pathogen-associated molecular patterns, such as bacterial endotoxin, bacterial genomic DNA, peptidoglycan, lipoteichoic acid, virus ssRNA, virus RNA and/or zymosan etc.

Above-mentioned fluids include human blood or blood plasma or drug injection or liquid biological reagent.

An adsorbing material for multiple pathogenic factors of sepsis is formed by coupling a ligand and a carrier, whose molecular structure is shown as follows

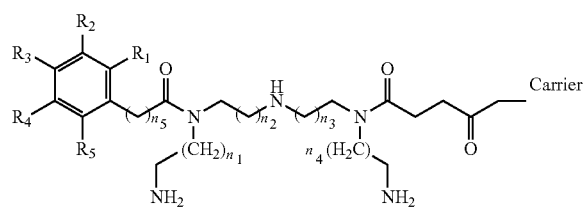

The carrier is amino-functionalized agarose or amino-functionalized polystyrene resin.

A preparation method of an adsorbing material for multiple pathogenic factors of sepsis has following steps:

1) In tetrahydrofuran or tetrahydrofuran aqueous solution or ethanol aqueous solution, compound 12 reacts with carrier M to generate compound 13, the mass ratio of compound 12 and carrier M is 0.01~1:100, reaction equation is:

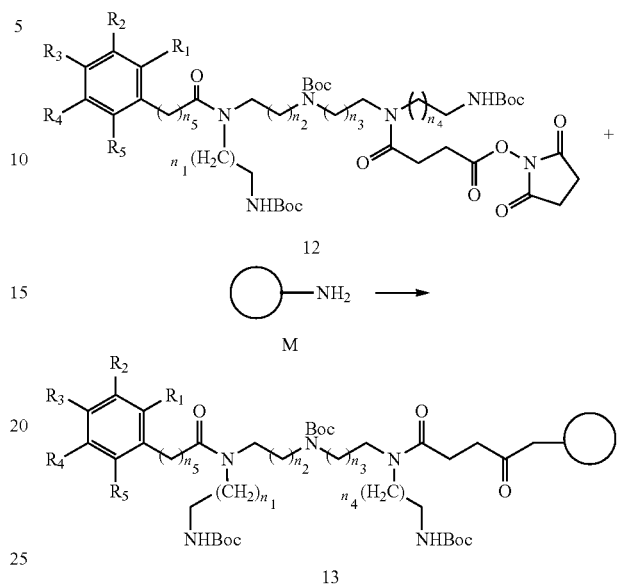

In N,N-Diisopropylethylamine, acetic anhydride is added into compound 13, and reacts with compound 13 to obtain crude product in which the residual amino of carrier are blocked, the equivalence ratio of compound 13 and acetic anhydride is 1:1~2, reaction equation is:

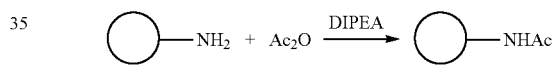

3) Preparation of end product

In methanol, 2~6M hydrochloric acid in methanol is added into the crude product in ice bath, the reaction generates the end product MTAM, the volume ratio of the crude product to hydrochloric acid in methanol is 1:0.5~1.5, reaction equation is:

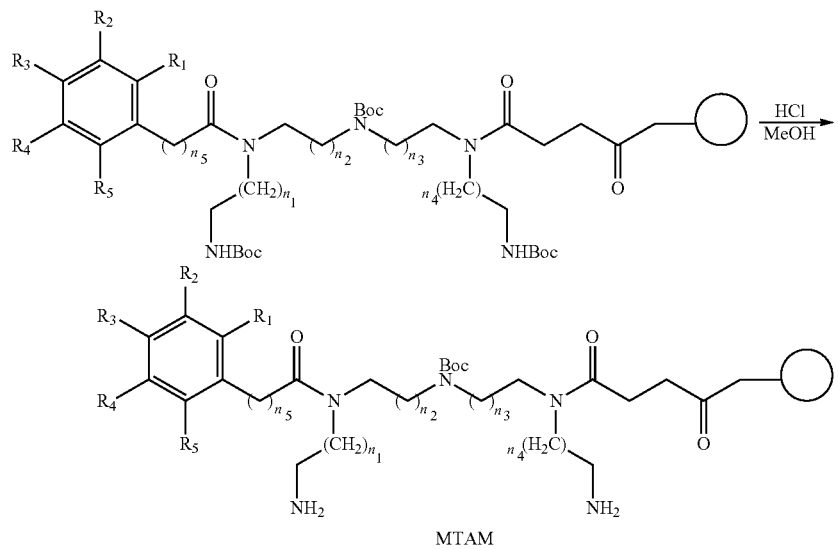

A use of the adsorbing material for multiple pathogenic factors of sepsis of the present invention in preparing a blood purification device for sepsis treatment, specifically for preparing an adsorption column in the blood purification device, is provided.

The results of experiments carried out by applicants show:

(1) The ligand is effectively coupled to the carrier through covalent coupling;

(2) The adsorbing material can significantly adsorb bacterial endotoxin, bacterial genomic DNA, peptidoglycan, lipoteichoic acid, virus RNA and zymosan in the blood plasma.

Pathogen-associated molecular patterns are main pathogenic factors that cause sepsis, it is very important for curing sepsis by eliminating these molecules from patient's body, no matter through drugs or blood purification therapies. In the present invention a novel ligand with adsorption effect on multiple pathogen-associated molecular patterns is coupled to the carrier, which could be agarose or polystyrene resin, these carriers are widely applied in clinical practice, and have been proved to have good blood compatibility. The material of the present invention is applied to the blood purification device, it can effectively adsorb bacterial endotoxin, bacterial genomic DNA, peptidoglycan, lipoteichoic acid, virus RNA and zymosan in blood, and has an important application prospect in blood purification for treatment of sepsis. Meanwhile, it should be understood by those skilled in the art that, according to the principle of use of the material of the present invention, the present invention could not only be applied in medical treatment but also be applied to remove bacterial endotoxin, bacterial genomic DNA, peptidoglycan, lipoteichoic acid, virus RNA and zymosan from solutions of drugs, biological reagents or the like.

DESCRIPTION OF THE DRAWINGS

FIGS. 5A-G are the results of static adsorption of bacterial endotoxin, bacterial genomic DNA, peptidoglycan, lipoteichoic acid, virus ssRNA, virus dsRNA and zymosan by the adsorbing material in blood plasma, wherein, 5A is the result of adsorption of bacterial endotoxin by adsorbing material, 5B is the result of adsorption of bacterial genomic DNA by adsorbing material, 5C is the result of adsorption of peptidoglycan by adsorbing material, 5D is the result of adsorption of lipoteichoic acid by adsorbing material, 5E is the result of adsorption of virus ssRNA by adsorbing material, 5F is the result of adsorption of virus dsRNA by adsorbing material, 5G is the result of adsorption of zymosan by adsorbing material;

FIGS. 6A-G are the results of dynamic adsorption of bacterial endotoxin, bacterial genomic DNA, peptidoglycan, lipoteichoic acid, virus ssRNA, virus dsRNA and zymosan by the adsorbing material in blood plasma. Wherein, 6A is the result of adsorpton of bacterial endotoxin by adsorbing material, wherein, 6B is the result of adsorption of bacterial genomic DNA by adsorbing material, 6C is the result of adsorption of peptidoglycan by adsorbing material, 6D is the result of adsorption of lipoteichoic acid by adsorbing material, 6E is the result of adsorption of virus ssRNA by adsorbing material, 6F is the result of adsorption of virus dsRNA by adsorbing material, 6G is the result of adsorption of zymosan by adsorbing material.

DETAILED DESCRIPTION

Figure 1:
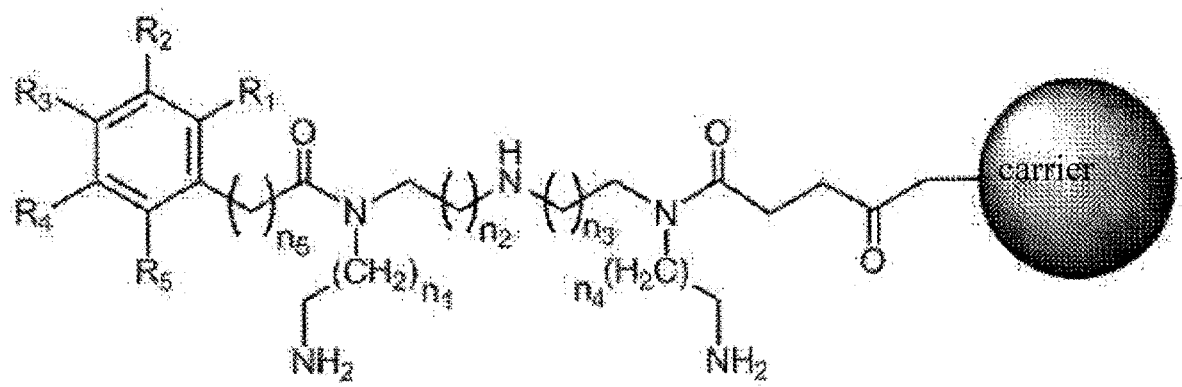
FIG. 1 is the schematic diagram of the molecular structure of the adsorbing material.

Following embodiments are only preferred embodiments to specify the present invention, which do not limit the present invention in any forms.

Chemical reagents used in embodiments were analytically pure purchased from Sigma-Aldrich Co. LLC. LPS, LTA and zymosan was purchased from Sigma-Aldrich Co. LLC, CpG DNA was purchased from Sangon Biotech (Shanghai) Co. LTD, PGN and virus RNA were purchased from InvivoGen Inc. Other reagents are commercially available analytical grade reagents without special description. English abbreviations in embodiments have following meaning.

| abbreviation | meaning | abbreviation | meaning |
| --- | --- | --- | --- |
| DCM | dichloromethane | $SOCl_2$ | Thionyl chloride |
| $Boc_2O$ | di-tert-butyl dicarbonate | $Et_3N$ | triethylamine |
| $MeOH/NH_3$ | saturated solution of ammonia in methanol | THF | tetrahydrofuran |
| RaneyNi | Raney nickel | $H_2O$ | water |
| $H_2$ | hydrogen | Pd/C | Palladium on carbon |
| MPa | Megapascal | $K_2CO_3$ | Potassium carbonate |
| EtOH | Ethanol | BnCl | benzyl chloride |
| DMF | N,N-Dimethylformamide | NaOH | sodium hydroxide |
| LPS | lipopolysaccharide | CpG DNA | bacterial genomic DNA |
| PGN | peptidoglycan | LTA | lipoteichoic acid |
| ssRNA | Single-stranded RNA | dsRNA | Double-stranded RNA |

Embodiment 1: Preparation of Ligand 1
1.1 Experimental Method
(1)
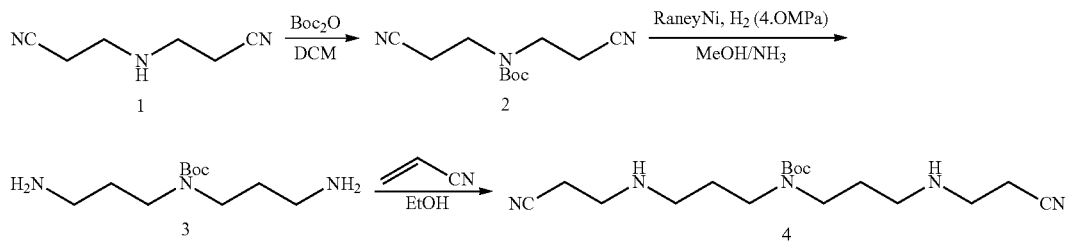
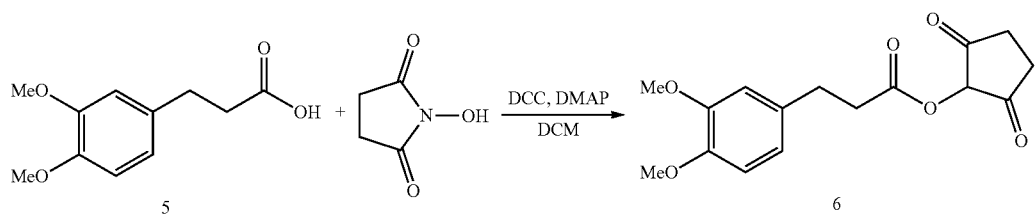
(2)
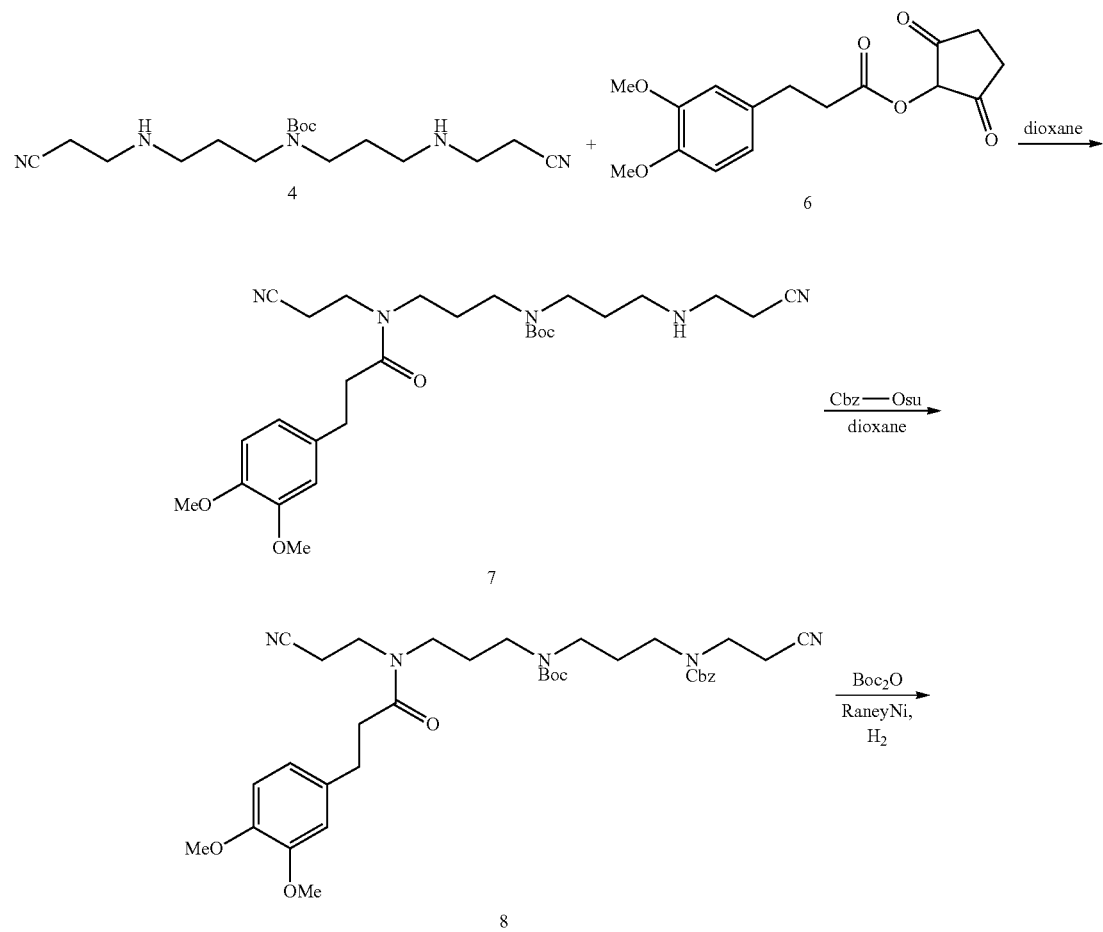
(3)

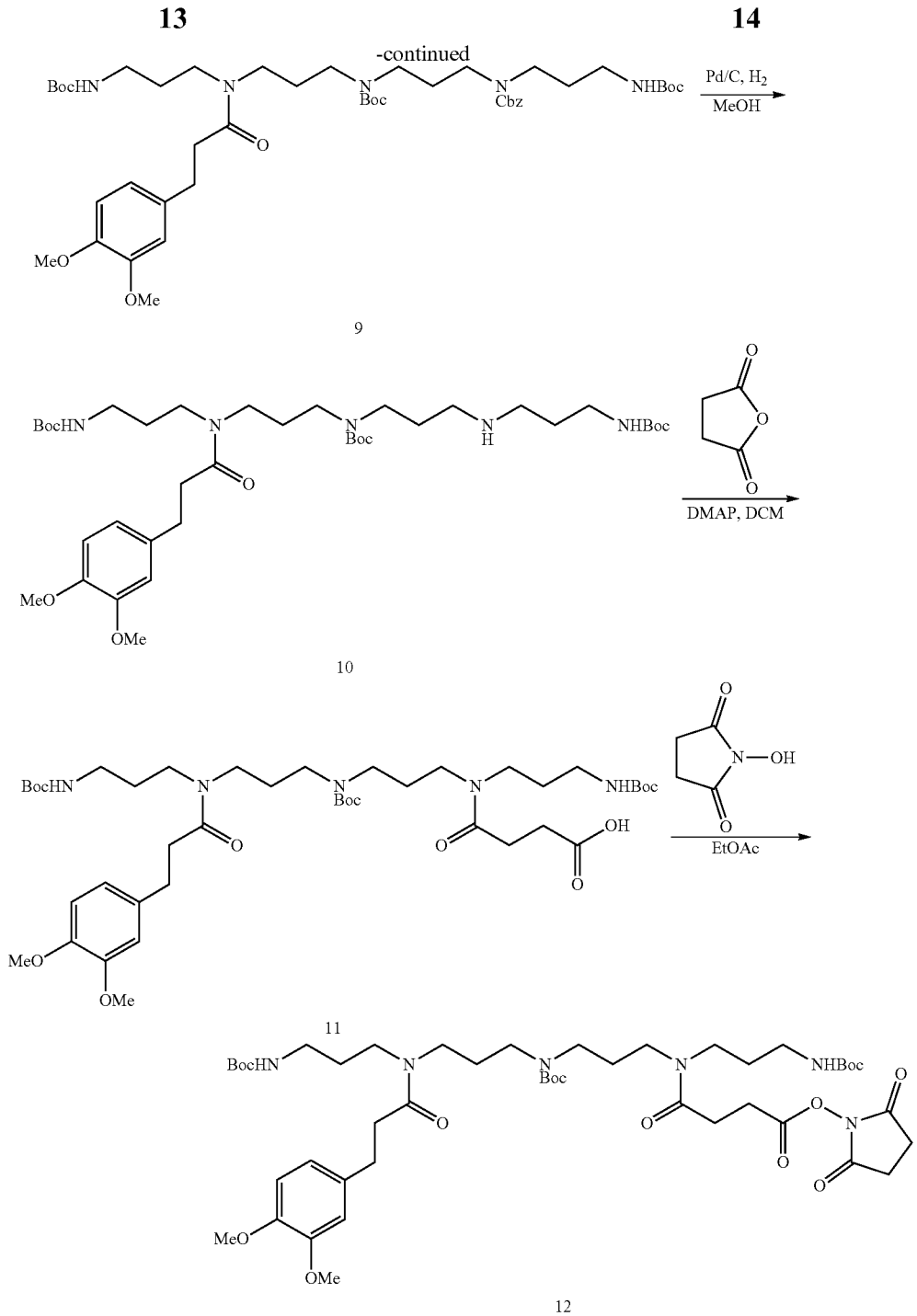

6 g of Di(2-cyanoethyl) amine (compound 1) was dissolved in 60 ml of dichloromethane under room temperature, and dichloromethane with equivalent amounts of di-tert-butyl dicarbonate was added dropwise to the solution, after 10 hours of reaction, the solution was dried by rotary evaporation, water and ethyl acetate was added for extracting for 3 times, the reaction solution was dried by anhydrous sodium sulfate, the solution was dried by rotary evaporation to obtain compound 2. 11 g of compound 2 was dissolved in 400 ml of saturated solution of ammonia in methanol, 1 g of raney nickel was added, the reactor was filled with hydrogen under the pressure of 4 MPa, after 72 hours of reaction under room temperature, the reaction solution was filtered and dried by rotary evaporation to obtain compound 3. 5.2 g of compound 3 was dissolved into 40 ml of ethanol, and 15 M acrylonitrile dissolved in ethanol was added dropwise in ice bath, after 10 hours of reaction at 40° C., the solution was dried by rotary evaporation to obtain compound 4. 4.2 g of 3,4-Dimethoxy hydrocinnamic acid (compound 5) was dissolved in dichloromethane, and 2.3 g N-Hydroxysuccinimide, 2.8 g dicyclohexylcarbodiimide and 0.5 g 4-dimethylaminopyridine was added, after 12 hours of reaction under room temperature, the reaction solution was filtered and dried by rotary evaporation to obtain compound 6. 2 g of compound 4 was dissolved in 15 ml of dioxane, and 1.76 g of compound 6 was added, after 24 hours of reaction at 50° C., compound 7 was obtained, then 1.48 g of N-(Benzyloxycarbonyloxy) succinimide was added, after 20 hours of reaction, water and ethyl acetate was added for extracting for 3 times, the reaction solution was dried by anhydrous sodium sulfate and rotary evaporation to obtain compound 8. 1 g of compound 8 was dissolved in ethanol, 1 g of di-tert-butyl dicarbonate and 0.1 g of raney nickel was added, the reactor was filled with hydrogen under the pressure of 2 MPa, after 48 hours of reaction at 45° C., the reaction solution was filtered and dried by rotary evaporation to obtain compound 9. 0.44 g of compound 9 was dissolved in methanol, 45 mg of palladium on carbon was added, and the reactor was filled with hydrogen, after 48 hours of reaction at 30° C., the reaction solution was filtered and dried by rotary evaporation to obtain compound 10. 0.4 g of compound 10 was dissolved in dichloromethane, 12 mg of 4-dimethylaminopyridine and 80 mg of succinic anhydride were added, after 48 hours of reaction at 25° C., the solution was dried by rotary evaporation to obtain compound 11, then 5 ml of ethyl acetate was added to dissolve it, and 93 mg of N-Hydroxysuccinimide was added, after 72 hours of reaction at 25° C., the solution was dried by rotary evaporation to obtain compound 12 (ligand 1).

1.2 Experimental Result ligand 1 was obtained, mass spectrum: [M+Na]$^+$ m/z=957.5; $^1$H NMR spectrum: 6.80-7.54 (m, 3H), 3.86 (s, 3H), 3.85 (s, 3H), 3.40 (brs, 2H), 3.34-3.28 (m, 3H), 3.23-3.21 (m, 2H), 3.15 (brs, 5H), 3.09-2.97 (m, 5H), 2.93-2.89 (m, 2H), 2.82 (brs, 4H), 2.74-2.64 (m, 3H), 2.59-2.57 (m, 2H), 1.90 (s, 2H), 1.81-1.75 (m, 5H), 1.65-1.63 (m, 3H), 1.44-1.41 (m, 27H), the chemical structure was identified as

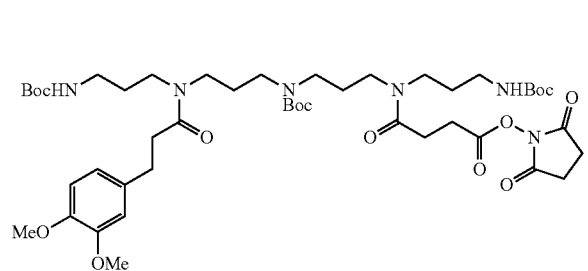 [SMILES: COc1ccc(CCC(=O)N(CCCNC(=O)OC(C)(C)C)CCCN(CCCN(CCCNC(=O)OC(C)(C)C)C(=O)CCC(=O)ON2C(=O)CCC2=O)C(=O)OC(C)(C)C)cc1OC]

Embodiment 2: Preparation of Ligand 2

2.1 Experimental Method the preparation method of embodiment 1 was employed, reaction is carried out under the same scale and condition, except that 3,4-Dimethoxyhydrocinnamic acid (compound 5) was replaced by Hydrocinnamic acid.

2.2 Experimental Result ligand 2 was obtained, mass spectrum: [M+Na]$^+$ m/z=897.5, the chemical structure was identified as

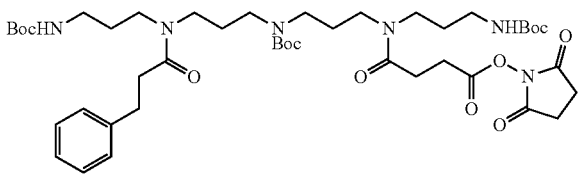 [SMILES: CC(C)(C)OC(=O)NCCCN(CCCN(CCCN(CCCNC(=O)OC(C)(C)C)C(=O)CCc1ccccc1)C(=O)OC(C)(C)C)C(=O)CCC(=O)ON1C(=O)CCC1=O]

Embodiment 3: Preparation of Ligand 3

3.1 Experimental Method the preparation method of embodiment 1 was employed, reaction was carried out under the same scale and condition, except that acrylonitrile was replaced by 3-Butene nitrile.

3.2 Experimental Result ligand 3 was obtained, mass spectrum: [M+Na]$^+$ m/z=985.5, the chemical structure was identified as

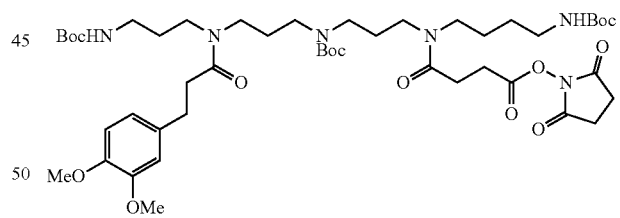

Embodiment 4: Preparation of Ligand 4

4.1 Experimental Method the preparation method of embodiment 1 was employed, reaction carried out under the same scale and condition, except that 3,4-Dimethoxyhydrocinnamic acid (compound 5) was replaced by 3,4-Dimethoxybenzoic acid.

4.2 Experimental Result ligand 4 was obtained, mass spectrum: [M+Na]⁺ m/z=929.5, the chemical structure was identified as

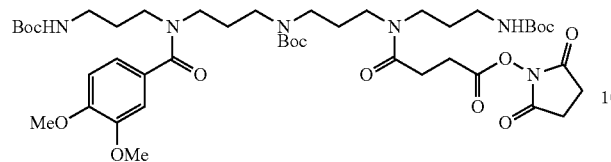

Embodiment 5: Preparation of Ligand 5

5.1 Experimental Method the preparation method of embodiment 1 was employed, reaction was carried out under the same scale and condition, except that Di(2-cyanoethyl) amine (compound 1) was replaced by Iminodiacetonitrile.

5.2 Experimental Result ligand 5 was obtained, mass spectrum: [M+Na]⁺ m/z=929.5, the chemical structure was identified as

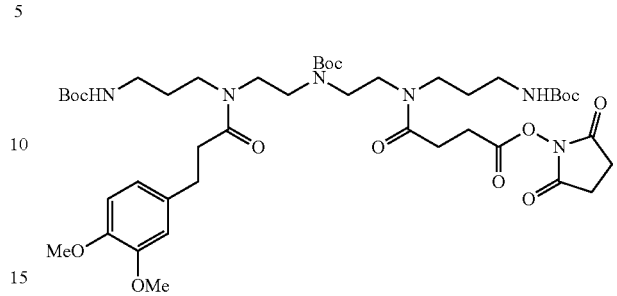

Embodiment 6: Preparation of Adsorbing Material for Multiple Pathogenic Factors (MTAM01S) of Sepsis with Agarose as Carrier

6.1 Experimental Method (1)
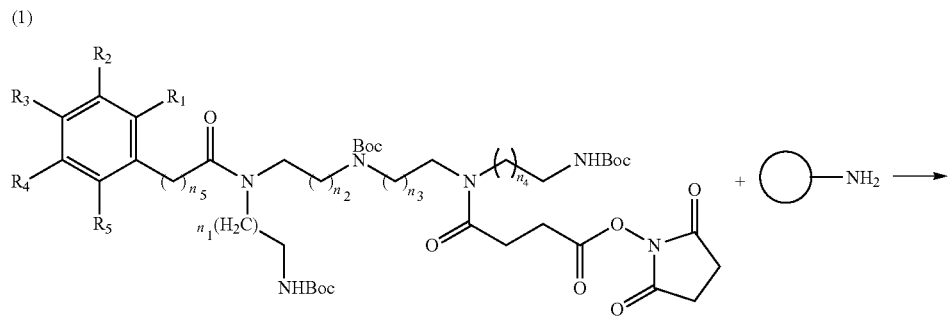

(2)
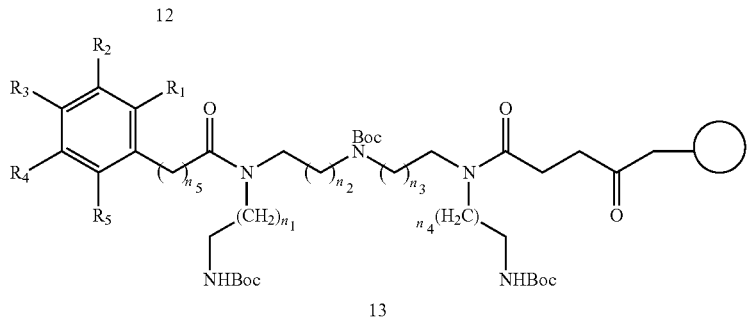

(3)
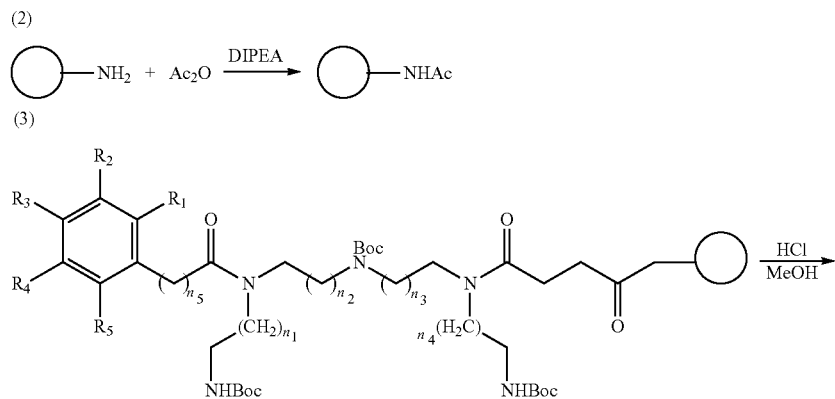

-continued

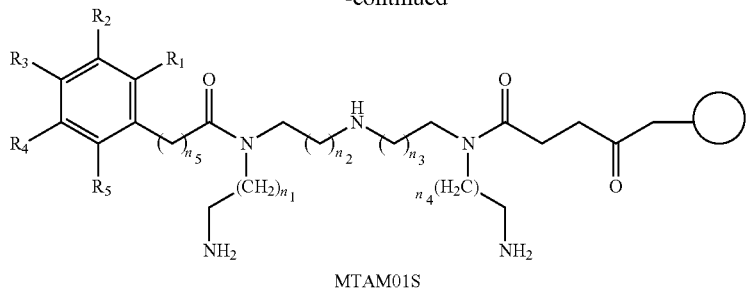

MTAM01S 5 ml of amino-functionalized agarose gel (purchased from Beijing wei shi bo hui chromatography technology co. LTD.) was dispersed in 2 ml of Tetrahydrofuran, then 2 mg of ligand 1 was dissolved into a small amount of Tetrahydrofuran and added dropwise in this solution, after 48 hours of reaction under room temperature, the reaction solution was filtered and washed with water to obtain compound 13. 0.5 ml of 10 mM N,N-Diisopropylethylamine was added in compound 13, then 0.8 ml of acetic anhydride was added, after 8 hours of reaction under room temperature, the reaction solution was filtered, and crude product of which the amino groups were blocked was obtained. The crude product was dissolved into 3 ml of methanol, 2 ml of 6 M hydrochloric acid in methanol was added dropwise into the solution in ice bath, after about 2 hours of reaction under room temperature, the reaction solution was filtered and washed with water to obtain the end product MTAM01S.

6.2 Experimental Result adsorbing material MTAM01S was obtained, and saved in 20% ethanol, structure was shown in FIG. 1, wherein the part of carrier was agarose gel.

Embodiment 7: Preparation of Adsorbing Material for Multiple Pathogen-Associated Molecular Patterns (MTAM01P) with Polystyrene Resin as Carrier 7.1 Experimental Method the preparation method of embodiment 6 was employed, reaction was carried out under the same scale and condition, except that amino-functionalized agarose gel was replaced by (Aminomethyl)poly(styrene-co-divinylbenzene) (purchased from Sigma-Aldrich)

7.2 Experimental Result adsorbing material MTAM01P was obtained, saved in 20% ethanol, structure was shown in FIG. 1, wherein the part of carrier was polystyrene resin.

Embodiment 8: The Static Adsorption of Bacterial Endotoxin (LPS) by MTAM01S and MTAM01P in Water 8.1 Experimental Method 0.5 ml of endotoxin (1 μg/ml) was isovolumetrically mixed with 0.5 ml of agarose resin (S carrier), polystyrene resin (P carrier), MTAM01S or MTAM01P respectively, the mixture was shaken and the reaction was carried out for 1 hour at 37° C. The reaction solution was centrifuged to collect the supernatant for the quantitative determination of endotoxin. Detection method was referred to bacterial endotoxins test of Appendix XI E of Chinese Pharmacopoeia (Volume II) and literature "Wei Guo, Zheng Jiang. Analysis and countermeasure of influence factors of quantitative detection of bacterial endotoxin. Journal of Regional Anatomy and Operative Surgery, 2003, 12:215-216.". The experimental result was expressed by measured endotoxin value and converted to adsorption rate.

Figure 2:
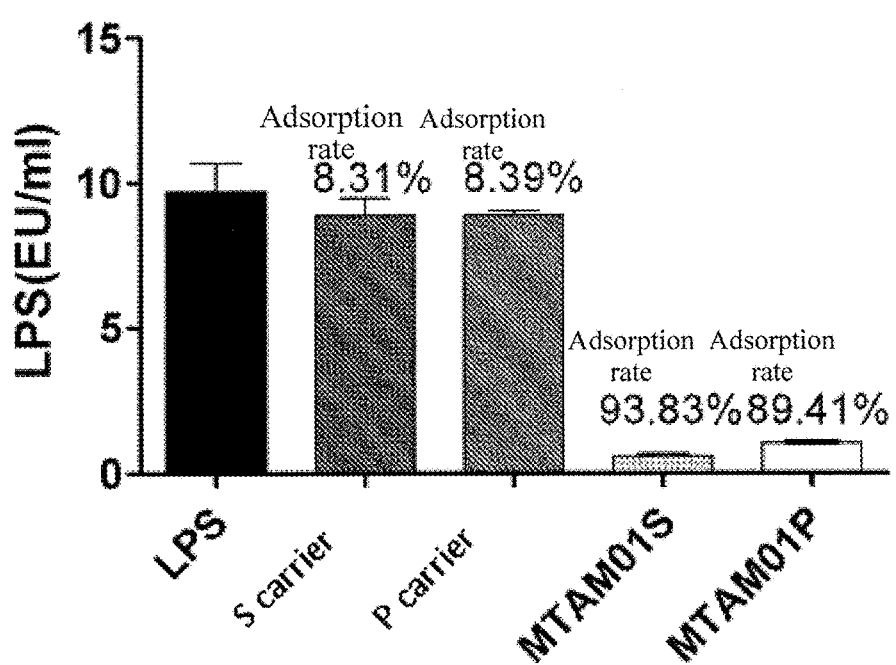
FIG. 2 is the result of static adsorption of bacterial endotoxin by the adsorbing material in water.

Experimental Result adsorption rate of the agarose and the polystyrene resin on endotoxin in water were only 8.31% and 8.39%, indicating the carriers themselves almost had no adsorption capacity. MTAM01S and MTAM01P have good adsorption activity on endotoxin, the adsorption rates reached to 93.83% and 89.41% respectively, the results were shown in FIG. 2.

Embodiment 9: The Static Adsorption of Bacterial Endotoxin (LPS) by MTAM01S and MTAM01P in Blood Plasma 9.1 Experimental Method 0.5 ml of endotoxin (1 μg/ml) dissolved in human blood plasma was isovolumetrically mixed with 0.5 ml of agarose resin (S carrier), polystyrene resin (P carrier), MTAM01S or MTAM01P respectively, the mixture was shaken and the reaction was carried out for 1 hour at 37° C. The reaction solution was centrifuged to collect the supernatant for the quantitative determination of endotoxin. Detection method was the same as embodiment 8. The experimental result was expressed by measured endotoxin value and converted to adsorption rate.

Figure 3:
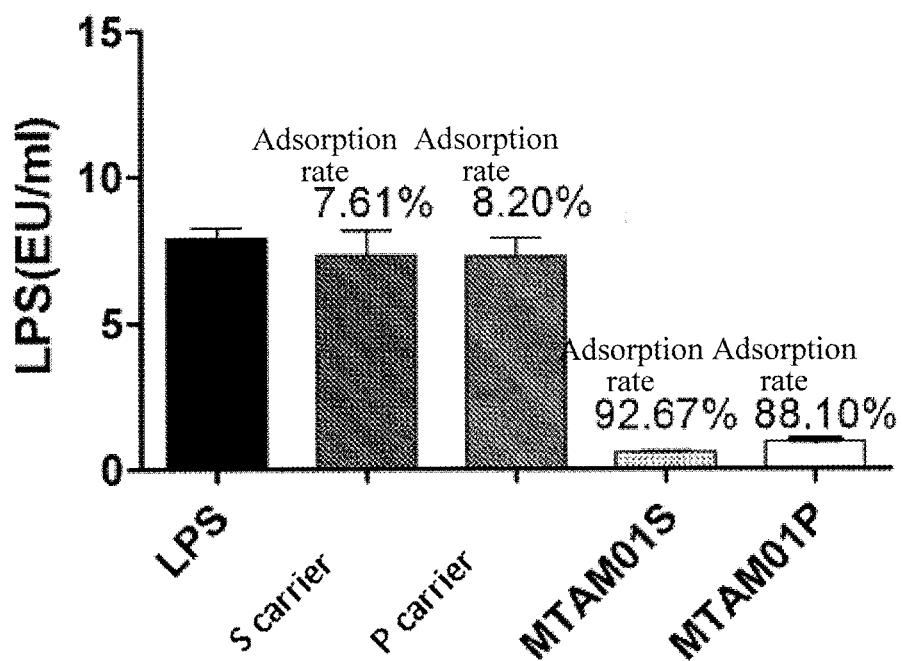
FIG. 3 is the result of static adsorption of bacterial endotoxin by the adsorbing material in blood plasma.

9.2 Experimental Result adsorption rate of the agarose and the polystyrene resin on endotoxin in blood plasma were only 7.61% and 8.20%, indicating the carriers themselves almost had no adsorption capacity. MTAM01S and MTAM01P had good adsorption activity on endotoxin in blood plasma, the adsorption rates reached to 92.67% and 88.10% respectively, the result was shown in FIG. 3.

Embodiment 10: The Dynamic Adsorption of Bacterial Endotoxin (LPS) by MTAM01S and MTAM01P in Blood Plasma 10.1 Experimental Method 10 ml of agarose resin (S carrier), polystyrene resin (P carrier), MTAM01S or MTAM01P were separately added into a chromatographic column with a diameter of 3 cm and a height of 15 cm, 10 ml of endotoxin (1 µg/ml) dissolved in human blood plasma was loaded on the column, and then the percolate was repeatedly loaded for 8 times, the level of endotoxin in each percolate was detected. Detection method is the same as embodiment 8. The experimental result was expressed by measured endotoxin value and converted to adsorption rate.

Figure 4:
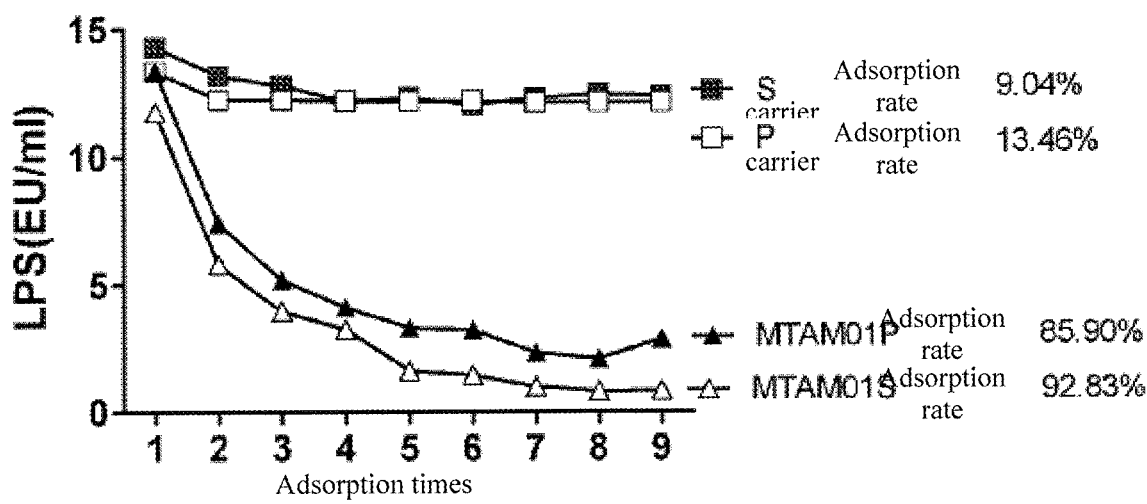
FIG. 4 is the result of dynamic adsorption of bacterial endotoxin by the adsorbing material in blood plasma.

10.2 Experimental Result the agarose and polystyrene resin almost has no adsorption capacity on endotoxin, but MTAM01S and MTAM01P had good adsorption effects on endotoxin, and the adsorption effect was in proportion to times of adsorption, the final adsorption rates reached to 92.83% and 85.90% respectively, the results were shown in FIG. 4.

Embodiment 11: The Static Adsorption of Bacterial Endotoxin (LPS), Bacterial Genomic DNA (CpG DNA), Peptidoglycan (PGN), Lipoteichoic Acid (LTA), Virus ssRNA, Virus dsRNA and Zymosan by MTAM01S and MTAM01P in Blood Plasma 11.1 Experimental Method 0.5 ml of bacterial endotoxin (1 µg/ml), Bacterial genomic DNA (10 µg/ml), peptidoglycan (10 µg/ml), lipoteichoic acid (10 µg/ml), virus ssRNA (10 µg/ml), virus dsRNA (10 µg/ml) or zymosan (10 µg/ml) dissolved in human blood plasma, were separately isovolumetrically mixed with 0.5 ml of agarose resin (S carrier), polystyrene resin (P carrier), MTAM01S or MTAM01P, the mixture was shaken and the reaction was carried out for 1 hour at 37° C. The reaction solution was centrifuged and 20 µl of the supernatant was collected and added into murine macrophage RAW 264.7 cells ($1 \times 10^6$/ml) cultured in vitro, after 12 hours of incubation, the stimulation of inflammatory cells by blood plasma that includes pathogen-associated molecular patterns before and after adsorption was detected. The detailed detection method was carried out according to the operating manual of mouse ELISA kit of eBioscience, the main steps included: ① the supernatant of RAW 264.7 cell culture medium was added into 96-well plate coated with capture antibody, and incubated for 2 hours under room temperature, washed 5 times with PBS; ② primary antibody marked with biotin was added, and incubated for 1 hour under room temperature, washed 5 times with PBS; ③ Horseradish Peroxidase marked with avidin was added, and incubated for half an hour under room temperature, washed 5 times with PBS; ④ coloring solution was added, and incubated for 10 minutes at 37° C., then stop solution was added; ⑤ Optical density value was measured by microplate reader at 450 nm wavelength. Experimental result reflected the adsorption capacity of adsorbing materials on pathogen-associated molecular patterns by inhibition ratio of TNF-α release in inflammatory cells.

11.2 Experimental Result the agarose and polystyrene resin had no absorption effects on any pathogen-associated molecular patterns, manifesting as no inhibiting effect on TNF-α release in RAW 264.7 cells stimulated by pre- and post-treatment of blood plasma. However the stimulation of inflammatory cells by blood plasma was significantly attenuated after the treatment of MTAM01S and MTAM01P, indicating that after the adsorption by MTAM01S and MTAM01P, the level of pathogen-associated molecular patterns in blood plasma was significantly reduced. Results were shown in FIG. 5, wherein, FIG. 5A was adsorption of bacterial endotoxin (LPS) by MTAM01S and MTAM01P, FIG. 5B was adsorption of bacterial genomic DNA (CpG DNA) by MTAM01S and MTAM01P, FIG. 5C was adsorption of peptidoglycan (PGN) by MTAM01S and MTAM01P, FIG. 5D was adsorption of lipoteichoic acid (LTA) by MTAM01S and MTAM01P, FIG. 5E was adsorption of virus ssRNA by MTAM01S and MTAM01P, FIG. 5F was adsorption of virus dsRNA by MTAM01S and MTAM01P, FIG. 5G was adsorption of zymosan by MTAM01S and MTAM01P.

Embodiment 12: The Dynamic Adsorption of Bacterial Endotoxin (LPS), Bacterial Genomic DNA (CpG DNA), Peptidoglycan (PGN), Lipoteichoic Acid (LTA), Virus ssRNA, Virus dsRNA and Zymosan by MTAM01S and MTAM01P in Blood Plasma 12.1 Experimental Method 10 ml of agarose resin (S carrier), polystyrene resin (P carrier), MTAM01S or MTAM01P were separately added into a chromatographic column with a diameter of 3 cm and a height of 15 cm, 10 ml of endotoxin (1 ug/ml), bacterial genomic DNA (10 µg/ml), peptidoglycan (10 µg/ml), lipoteichoic acid (10 µg/ml), virus ssRNA (10 µg/ml), virus dsRNA (10 µg/ml) and zymosan (10 µg/ml) dissolved in human blood plasma were loaded on the column, then it's the percolate was repeatedly loaded for 5 times, 20 µl of the first, third and fifth percolates were added into RAW 264.7 cells, the stimulation effect of inflammatory cells by blood plasma containing pathogen-associated molecular patterns before and after adsorption was detected according to the method described in embodiment 11.

12.2 Experimental Result the agarose resin and polystyrene resin had no absorption effect on any pathogen-associated molecular patterns, MTAM01S and MTAM01P could significantly adsorb various pathogen-associated molecular patterns, manifesting as the stimulation of inflammatory cells by blood plasma was significantly attenuated after absorption (significant decrease in release of TNF-α), indicating that after adsorption of MTAM01S and MTAM01P, the level of pathogen-associated molecular patterns in blood plasma was significantly reduced, results were shown in FIG. 6. Wherein, FIG. 6A was adsorption of bacterial endotoxin (LPS) by MTAM01S and MTAM01P, FIG. 6B was adsorption of bacterial genomic DNA (CpG DNA) by MTAM01S and MTAM01P, FIG. 6C was adsorption of peptidoglycan (PGN) by MTAM01S and MTAM01P, FIG. 6D was adsorption of lipoteichoic acid (LTA) by MTAM01S and MTAM01P, FIG. 6E was adsorption of virus ssRNA by MTAM01S and MTAM01P, FIG. 6F was adsorption of virus dsRNA by MTAM01S and MTAM01P, FIG. 6G was adsorption of zymosan by MTAM01S and MTAM01P.

Embodiment 13: The Static Adsorption of Bacterial Lysate (Mixture of Multiple Pathogen-Associated Molecular Patterns) by MTAM01S and MTAM01P 13.1 Experimental Method the cultured *Escherichia coli* and *Staphylococcus aureus* was separately added with Lysis Buffer (50 mM Tris pH 8.0, 10% glycine, 0.1% triton-X100, 100 ug/ml Lysozyme, 1 mM PMSF) in a volume ratio of 2:1, broke down the cell membrane by sonication (3 times, 20 seconds for each), the bacterial cleavage product treated by sonication was diluted with human blood plasma, the concentration was $1\times10^8$ CFU/ml (*Escherichia coli*) and $5\times10^8$ CFU/m (*Staphylococcus aureus*) according to bacteria count. The cleavage products were isovolumetrically mixed with 0.5 ml of agarose resin (S carrier), polystyrene resin (P carrier), MTAM01S or MTAM01P, respectively, the mixture was shaken and the reaction was carried out for 1 hour at 37° C. The reaction solution was centrifuged and 20 μl of supernatant was collected and added into murine macrophage RAW 264.7 cells ($1\times10^6$/ml) cultured in vitro, after 12 hours of incubation, the stimulation of inflammatory cells by blood plasma before and after adsorption was detected, detection method was the same as embodiment 11.

Figures 7A, 7B:
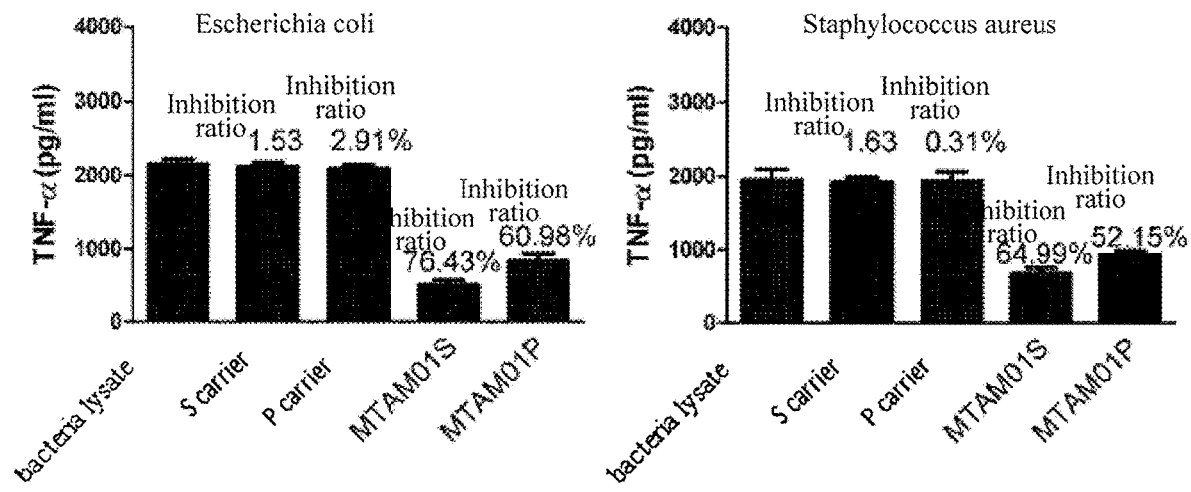
FIGS. 7A and 7B are the results of static adsorption of bacterial lysate (mixture of multiple pathogen-associated molecular patterns) by adsorbing material; wherein, 7A is the result of adsorption of *Escherichia coli* lysate by adsorbing material, 7B is the result of adsorption of *Staphylococcus aureus* lysate by adsorbing material.

13.2 Experimental Result the agarose resin and polystyrene resin themselves had no absorption effect on various bacterial pathogen-associated molecular patterns, MTAM01S and MTAM01P had good adsorption activity on pathogen-associated molecules mixture derived from *Escherichia coli* (gram-negative bacteria) and *Staphylococcus aureus* (gram-positive bacteria), manifesting as stimulating activity of inflammatory cells by bacterial lysate significantly attenuated after adsorption of MTAM01S and MTAM01P (significant decrease in release of TNF-α), results were shown in FIG. 7. Wherein, FIG. 7A was adsorption of *Escherichia coli* lysate by MTAM01S and MTAM01P, FIG. 7B was adsorption of *Staphylococcus aureus* lysate by MTAM01S and MTAM01P.

Embodiment 14: The Dynamic Adsorption of Bacteria Lysate (Mixture of Multiple Pathogen-Associated Molecular Patterns) by MTAM01S and MTAM01P 14.1 Experimental Method 10 ml of agarose resin (S carrier), polystyrene resin (P carrier), MTAM01S or MTAM01P were separately added into a chromatographic column with a diameter of 3 cm and a height of 15 cm. The *Escherichia coli* and *Staphylococcus aureus* lysate were prepared according to the method of embodiment 10. 10 ml of bacterial lysate diluted with human blood plasma was loaded on the column, then the percolate was repeatedly loaded for 5 times, 20 μl of the first, third and fifth percolates were added into RAW 264.7 cells, the stimulation effect of inflammatory cells by bacteria lysate before and after adsorption was detected according to the method described in embodiment 11.

Figure 8A:
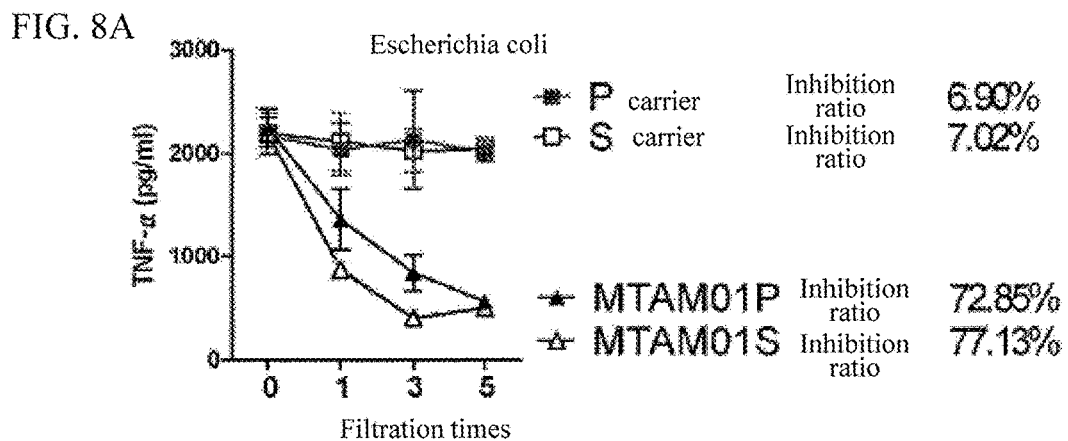
FIGS. 8A and 8B are the results of dynamic adsorption of bacterial lysate (mixture of multiple pathogen-associated molecular patterns) by adsorbing material. Wherein, 8A is the result of adsorption of *Escherichia coli* lysate by adsorbing material. 8B is the result of adsorption of *Staphylococcus aureus* lysate by adsorbing material.
Figure 8B:
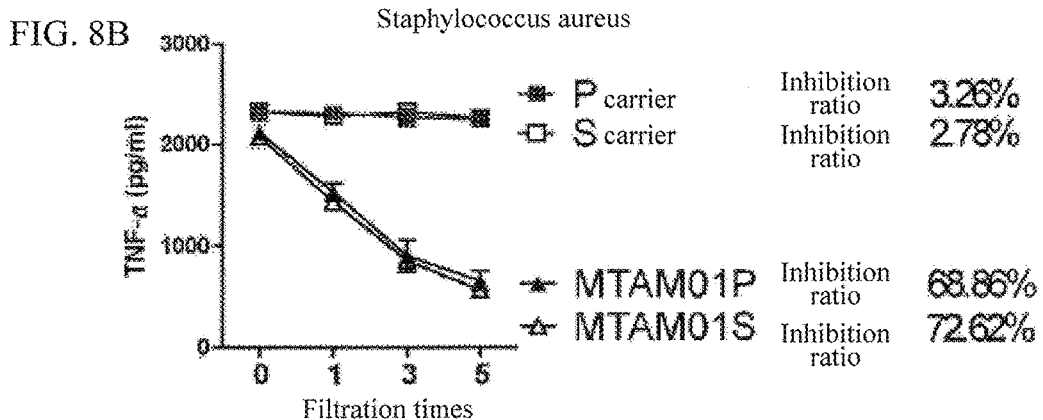

14.2 Experimental Result the agarose resin and polystyrene resin themselves had no absorption effect on various pathogen-associated molecular patterns, MTAM01S and MTAM01P were capable of adsorbing the mixture of pathogen-associated molecular patterns derived from *Escherichia coli* (gram-negative bacteria) and *Staphylococcus aureus* (gram-positive bacteria), manifesting as stimulating activity of inflammatory cells by bacterial lysate significantly attenuated after adsorption of MTAM01S and MTAM01P (significant decrease in release of TNF-α), results were shown in FIG. 8. Wherein, FIG. 8A was adsorption of *Escherichia coli* lysate by MTAM01S and MTAM01P, FIG. 8B was adsorption of *Staphylococcus aureus* lysate by MTAM01S and MTAM01P.

Embodiment 15: Preparation of Adsorbing Material Based on Ligands 2~5

15.1 Experimental Method the preparation method of embodiment 6 was employed, reaction was carried out under the same scale and condition, except that ligand 1 was replaced by ligand 2, ligand 3, ligand 4 or ligand 5, and ligand 2~5 was coupled with amino-functionalized agarose gel or amino-functionalized polystyrene resin respectively.

15.2 Experimental Method below-mentioned adsorbing materials were obtained: an adsorbing material MTAM02S with agarose gel as carrier, ligand 2 as ligand; an adsorbing material MTAM03S with agarose gel as carrier, ligand 3 as ligand; an adsorbing material MTAM04S with agarose gel as carrier, ligand 4 as ligand; an adsorbing material MTAM05S with agarose gel as carrier, ligand 5 as ligand; an adsorbing material MTAM02P with polystyrene resin as carrier, ligand 2 as ligand; an adsorbing material MTAM03P with polystyrene resin as carrier, ligand 3 as ligand; an adsorbing material MTAM04P with polystyrene resin as carrier, ligand 4 as ligand; an adsorption material MTAM05P with polystyrene resin as carrier, ligand 5 as ligand.

Embodiment 16: The Dynamic Adsorption of Bacterial Endotoxin (LPS), Bacterial Genomic DNA (CpG DNA), Peptidoglycan (PGN), Lipoteichoic Acid (LTA), Virus ssRNA, Virus dsRNA and Zymosan by MTAM02~05S as Well as MTAM02~05P in Blood Plasma 16.1 Experimental Method the preparation method of embodiment 12 was employed, reaction was carried out under the same scale and condition, except that adsorbing material MTAM01S and MTAM01P were replaced by MTAM02~05S and MTAM02~05P, respectively.

16.2 Experimental Result

MTAM02~05S and MTAM02~05P were capable of adsorbing various pathogen-associated molecular patterns, manifesting as stimulating activity of inflammatory cells by blood plasma significantly attenuated after adsorption (significant decrease in release of TNF-α). After being filtered for 5 times, the inhibition ratio of TNF-α release in inflammatory cells stimulated by pathogen-associated molecular patterns was used to represent the adsorption of pathogen-associated molecular patterns by adsorbing material, results were showed in table 1.

TABLE 1 the detection of adsorption capacity of MTAM02~05S as well as MTAM02~05P

| Pathogen-associated Adsorbing molecular patterns material | LPS | CpG DNA | PGN | LTA | virus ssRNA | virus dsRNA | Zymosan |
|---|---|---|---|---|---|---|---|
| MTAM02S | 92.6% | 80.4% | 84.3% | 76.8% | 64.3% | 65.9% | 70.7% |
| MTAM03S | 88.7% | 90.7% | 96.6% | 81.6% | 72.2% | 77.1% | 72.6% |
| MTAM04S | 94.4% | 85.2% | 88.6% | 80.1% | 78.6% | 70.6% | 68.9% |
| MTAM05S | 82.7% | 75.3% | 79.4% | 86.4% | 67.7% | 62.8% | 77.6% |
| MTAM02P | 71.6% | 81.5% | 75.6% | 85.3% | 83.4% | 76.2% | 69.7% |
| MTAM03P | 77.8% | 84.6% | 84.2% | 90.6% | 64.4% | 60.5% | 79.8% |
| MTAM04P | 64.9% | 69.4% | 78.6% | 66.5% | 52.3% | 60.9% | 74.6% |
| MTAM05P | 83.6% | 88.9% | 80.2% | 76.4% | 70.6% | 71.8% | 77.1% |

Above-mentioned experiments showed that adsorbing material of the present invention had significant absorption effects on bacterial endotoxin, bacterial genomic DNA, peptidoglycan, lipoteichoic acid, virus RNA and zymosan in fluid such as blood plasma and the like, the stimulation effect of immune cells by blood plasma was significantly attenuated after adsorption, the adsorbing material of the present invention was suitable for blood purification of sepsis patients.

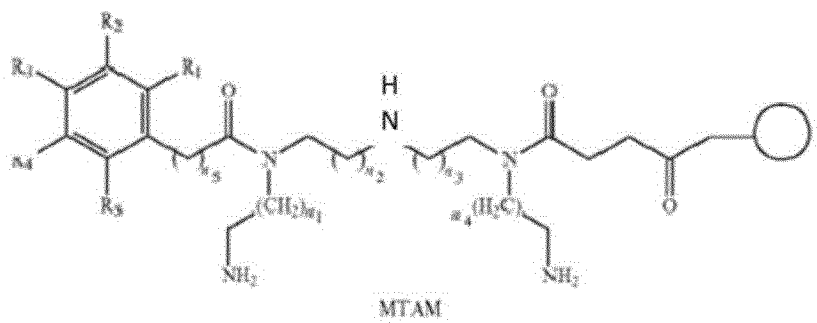

The invention claimed is:

1. A preparation method of a ligand of adsorbing materials for adsorbing multiple pathogenic factors of sepsis in fluids, comprising the following steps:

1) In dichloromethane, compound 1 reacts with di-tert-butyl dicarbonate to generate compound 2, reaction temperature is 20~30° C., the equivalence ratio of compound 1 and di-tert-butyl dicarbonate is 1:0.5~2, reaction equation is

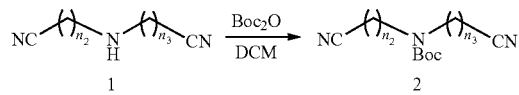

2) In a saturated solution of ammonia in methanol, compound 3 is generated from compound 2 through hydrogenation under the existence of raney nickel and hydrogen, reaction temperature is 20~50° C., pressure is 1~10 Mpa, the mass of raney nickel is 10%~50% of the mass of compound 2, reaction equation is:

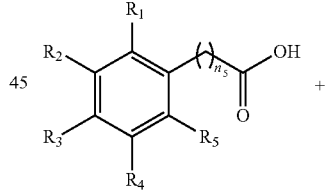

3) In ethanol or methanol, compound 3 reacts with α, β-unsaturated nitrile to generate compound 4, reaction temperature is 20~50° C., the equivalence ratio of compound 3 and α, β-unsaturated nitrile is 1:2~3, reaction equation is:

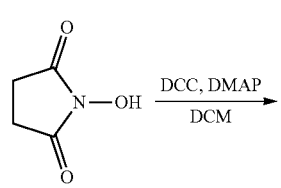

4) In dichloromethane, compound 5 reacts with N-Hydroxysuccinimide to generate compound 6 under the existence of N,N'-dicyclohexylcarbodiimide and 4-dimethylaminopyridine, reaction temperature is 20~30° C., the equivalence ratio of compound 5 and N-Hydroxysuccinimide is 1:1~2, reaction equation is:

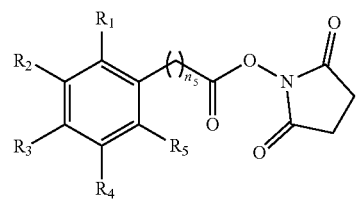

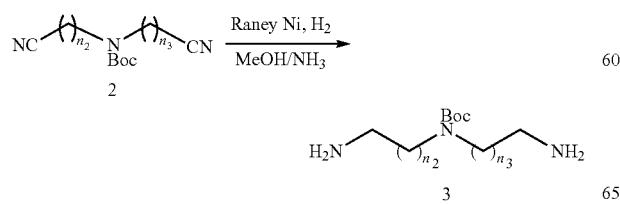

5) In dioxane, compound 4 reacts with compound 6 to generate compound 7, reaction temperature is 30~50° C., the equivalence ratio of compound 4 and compound 6 is 1:1~2, reaction equation is:

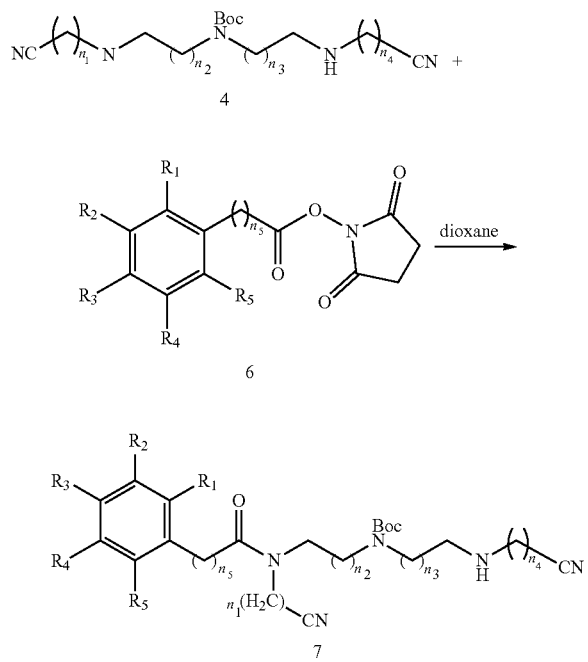

6) In dioxane, compound 7 reacts with N-Carbobenzoxyoxysuccinimide to generate compound 8, reaction temperature is 30~50° C., the equivalence ratio of compound 7 and N-Carbobenzoxyoxysuccinimide is 1:1~2, reaction equation is:

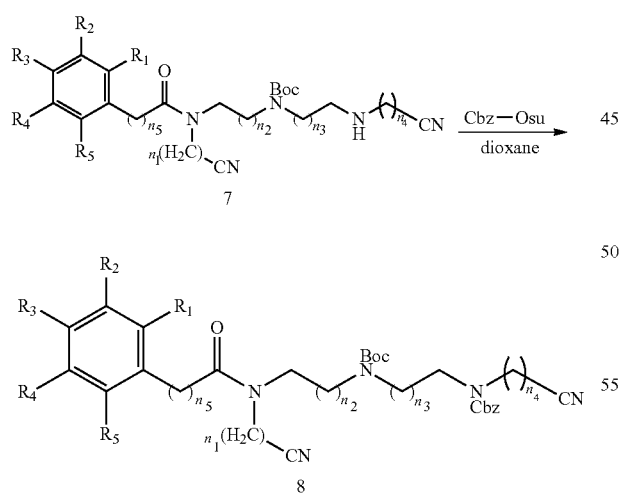

7) In ethanol or methanol, compound 8 reacts with di-tert-butyl dicarbonate to generate compound 9 under the existence of raney nickel and hydrogen, reaction temperature is 30~50° C., the equivalence ratio of compound 8 and di-tert-butyl dicarbonate is 1:0.5~3, pressure is 1~10 Mpa, the mass of the raney nickel is 10%~50% of the mass of compound 8, reaction equation is:

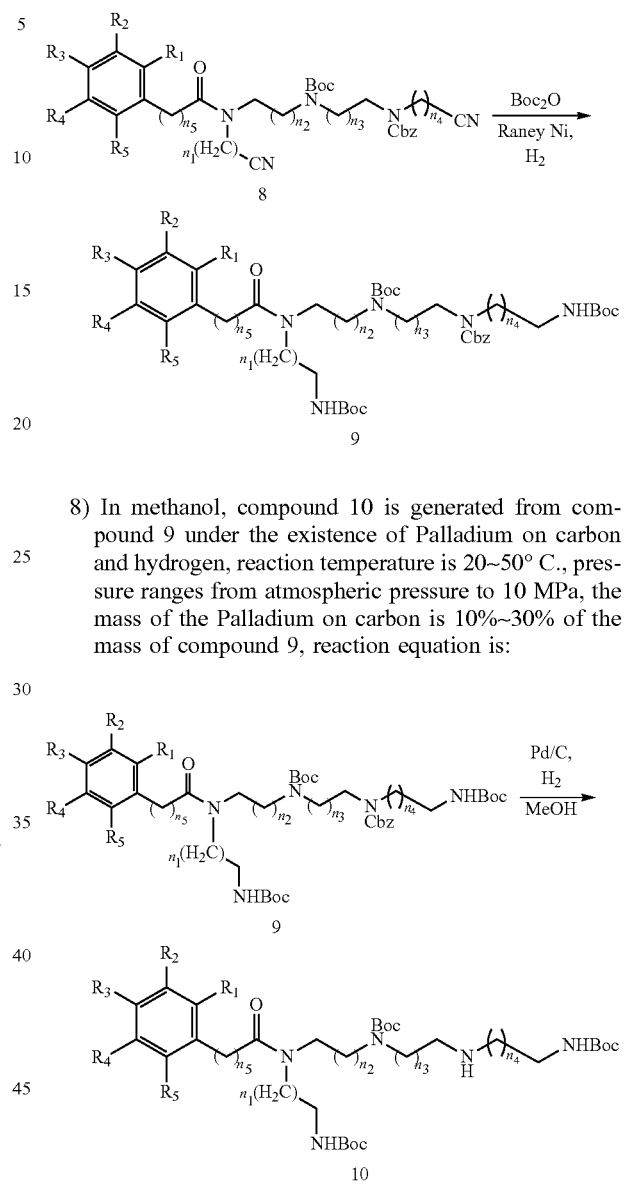

8) In methanol, compound 10 is generated from compound 9 under the existence of Palladium on carbon and hydrogen, reaction temperature is 20~50° C., pressure ranges from atmospheric pressure to 10 MPa, the mass of the Palladium on carbon is 10%~30% of the mass of compound 9, reaction equation is:

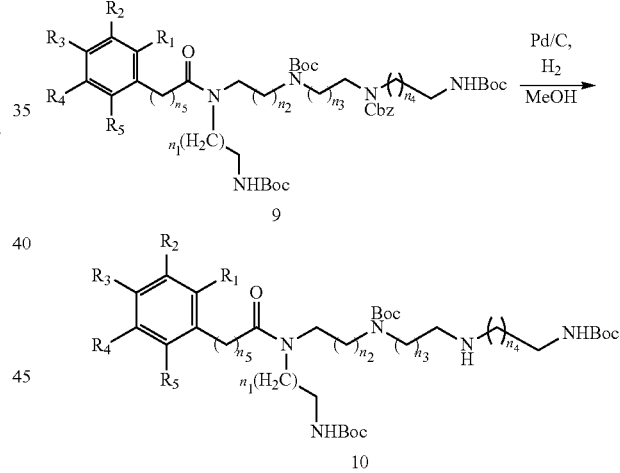

9) In dichloromethane, compound 10 reacts with succinic anhydride to generate compound 11 under the existence of 4-dimethylaminopyridine, reaction temperature is 20~30° C., the equivalence ratio of compound 10 and succinic anhydride is 1:1~2, reaction equation is:

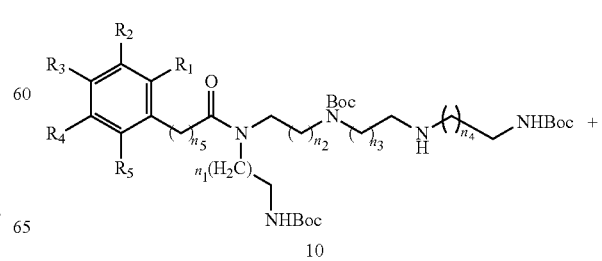

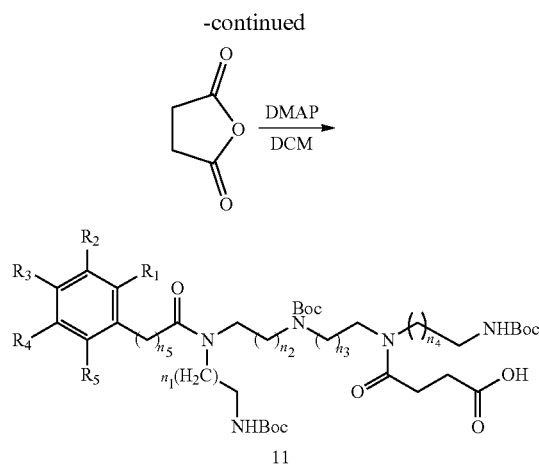

10) In ethyl acetate, compound 11 reacts with N-Hydroxysuccinimide to generate compound 12, reaction temperature is 20~30° C., the equivalence ratio of compound 11 and N-Hydroxysuccinimide is 1:1~2, reaction equation is:

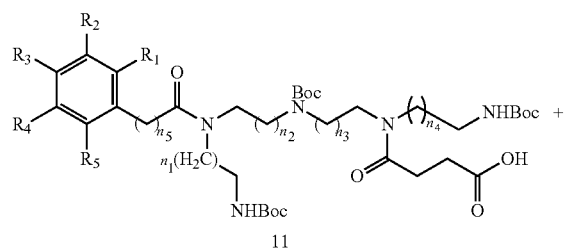

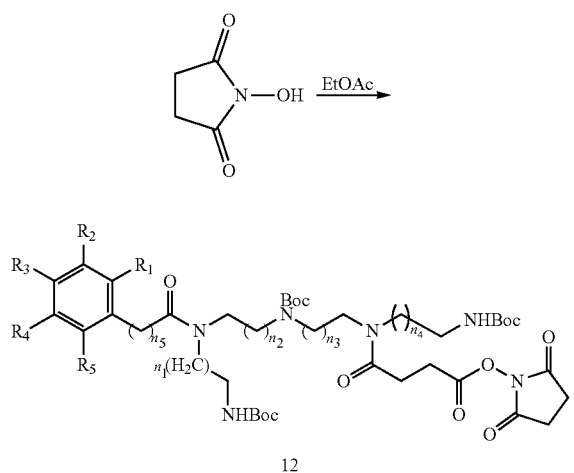

wherein $n_1$-$n_4$ is an integer between 1-6, and $n_5$ is an integer between 0-3.

2. The method according to claim 1, wherein the multiple pathogenic factors of sepsis include bacterial endotoxin, bacterial genomic DNA, peptidoglycan, lipoteichoic acid, virus RNA and/or zymosan.

3. The method according to claim 1, wherein the fluids include human blood or blood plasma or drug injection or liquid biological reagent.

4. An adsorbing material for multiple pathogenic factors of sepsis, wherein the material is formed by coupling the ligand prepared through the method of claim 1 and a carrier, whose molecular structure is shown as follows

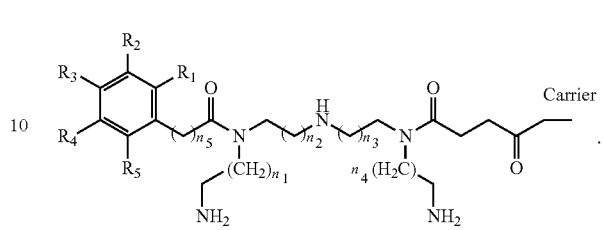

5. The adsorbing material according to claim 4, wherein the carrier is amino-functionalized agarose or amino-functionalized polystyrene resin.

6. A preparation method of an adsorbing material for adsorbing multiple pathogenic factors of sepsis, comprising following steps:
   1) In tetrahydrofuran or tetrahydrofuran aqueous solution or ethanol aqueous solution, compound 12 reacts with carrier M to generate compound 13, the mass ratio of compound 12 and carrier M is 0.01~1:100, reaction equation is:

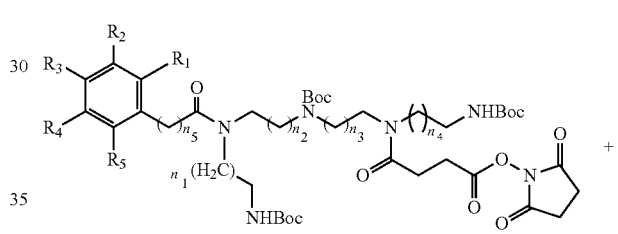

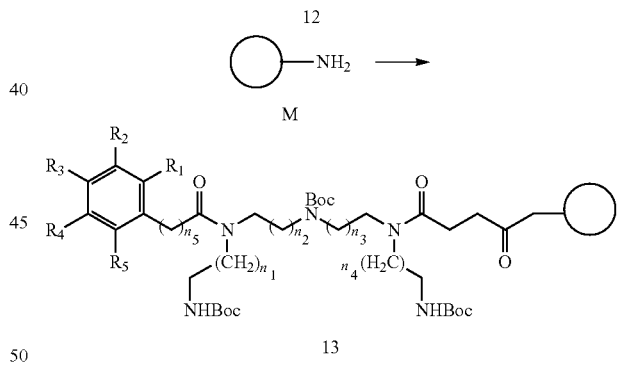

2) Blockade of residual amino of carrier:
In N,N-Diisoprolethylaamine, acetic anhydride is added into compound 13, and reacts with compound 13 to obtain crude product in which the residual amino of carrier are blocked, the equivalence ratio of compound 13 and acetic anhydride is 1:1~2, reaction equation is:

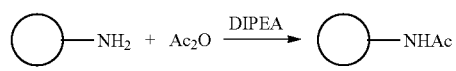

3) Preparation of end product:
In methanol, 2~6M hydrochloric acid in methanol is added into the crude product in ice bath, the reaction generates the end product MTAM, the volume ratio of the crude product to hydrochloric acid in methanol is 1:0.5~1.5, reaction equation is:
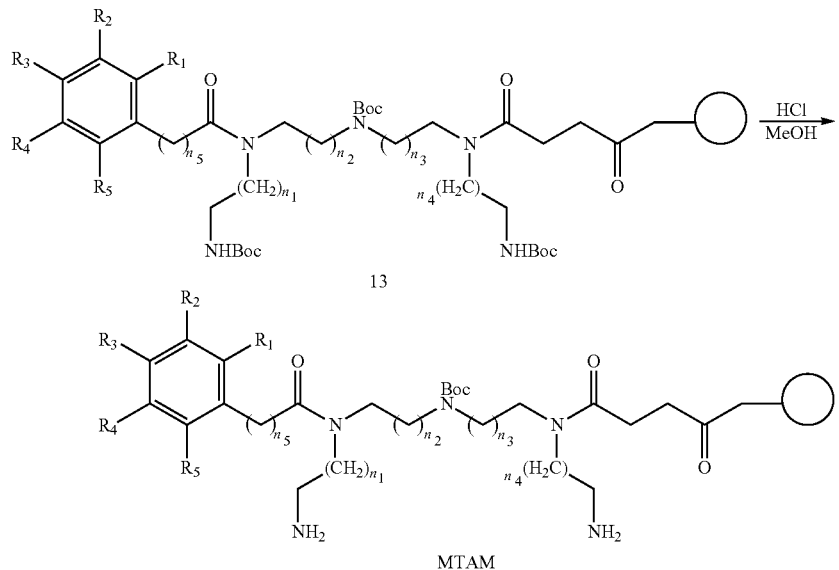
wherein $n_1$-$n_4$ is an integer between 1-6, and $n_5$ is an integer between 0-3.
7. A blood purification device for treatment of sepsis comprising the adsorbing material according to claim 4.
8. A blood purification device for treatment of sepsis comprising the adsorbing material according to claim 5.
* * * * *

UNITED STATES PATENT AND TRADEMARK OFFICE
CERTIFICATE OF CORRECTION

PATENT NO. : 10,898,632 B2
APPLICATION NO. : 15/770629
DATED : January 26, 2021
INVENTOR(S) : Yue Zheng et al.

Page 1 of 2

It is certified that error appears in the above-identified patent and that said Letters Patent is hereby corrected as shown below:

In Column 27, Line 10 (Claim 1):

"
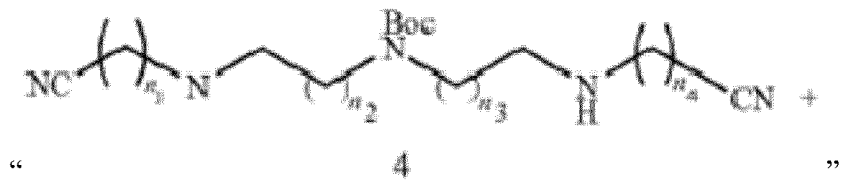
"

Should read:

--
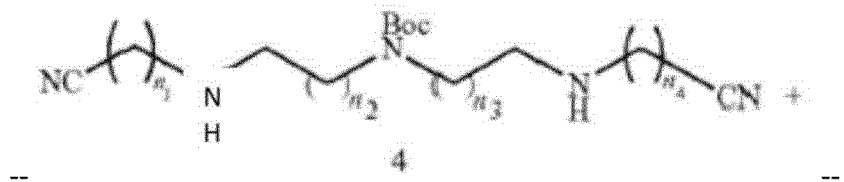
--

In Column 31, Line 27 (Claim 6):

"
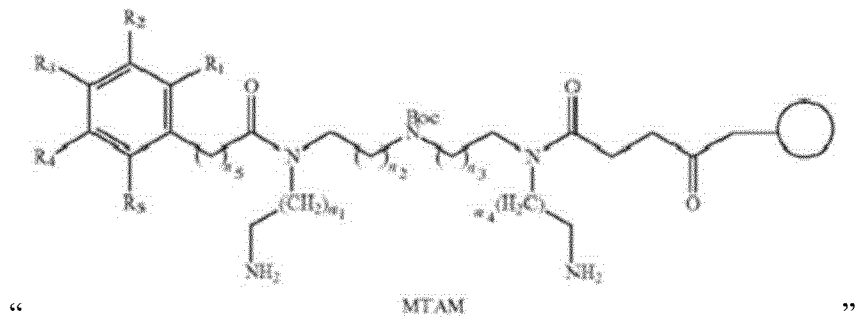
"

Should read:

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,898,632 B2